(12) United States Patent
Biellak et al.

(10) Patent No.: US 6,956,644 B2
(45) Date of Patent: *Oct. 18, 2005

(54) SYSTEMS AND METHODS FOR A WAFER INSPECTION SYSTEM USING MULTIPLE ANGLES AND MULTIPLE WAVELENGTH ILLUMINATION

(75) Inventors: Steve Biellak, Sunnyvale, CA (US); Stanley E. Stokowski, Danville, CA (US); Mehdi Vaez-Iravani, Los Gatos, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 568 days.

This patent is subject to a terminal disclaimer.

(21) Appl. No.: 09/891,693

(22) Filed: Jun. 26, 2001

(65) Prior Publication Data

US 2001/0052975 A1 Dec. 20, 2001

Related U.S. Application Data

(63) Continuation-in-part of application No. 09/746,141, filed on Dec. 21, 2000, now Pat. No. 6,639,662, which is a continuation of application No. 08/933,771, filed on Sep. 19, 1997, now Pat. No. 6,201,601.

(51) Int. Cl.[7] ............................................. G01N 21/00
(52) U.S. Cl. .................. 356/237.4; 356/237.5
(58) Field of Search .......................... 356/237.1–237.5, 356/239.1, 239.3, 239.7, 239.8, 338–339, 445; 250/559.04, 559.16, 237 R, 559.4

(56) References Cited

U.S. PATENT DOCUMENTS

| 4,449,818 A |   | 5/1984  | Yamaguchi            |
|-------------|---|---------|----------------------|
| 4,740,079 A | * | 4/1988  | Koizumi et al. ............ 356/237 |
| 4,794,265 A |   | 12/1988 | Quackenbos et al.    |

(Continued)

FOREIGN PATENT DOCUMENTS

| EP | 0624787       | 11/1994 |
| EP | 1 318 392 A1  | 10/2002 |
| GB | 4123916       | 1/1992  |
| WO | WO97/12226    | 4/1997  |
| WO | WO97/33158    | 9/1997  |
| WO | WO 00/02027   | 1/2000  |

OTHER PUBLICATIONS

Dialog Search conducted on Jul. 15, 2002.
Dialog Search conducted on Jul. 16, 2002.
International Search Report issued by the International Patent Office (WIPO) corresponding to the International Patent Application No.: PCT/US02/20881, issued on Sep. 23, 2002.
U.S. Appl. No. 09/746,141, filed Dec. 21, 2000.
"Surface Inspection System for Estimation of Wafer," Y. Yatsugake et al., *Hitachi Electronics Engineering Technical Report*, vol. 11, Jan. 1996, pp. 21–26.

(Continued)

*Primary Examiner*—Hoa Q. Pham
(74) *Attorney, Agent, or Firm*—Parsons Hsue & de Runtz LLP

(57) ABSTRACT

A method for detecting an anomaly on a top surface of a substrate comprises directing a first radiation beam having a first wavelength at the top surface of the substrate at a first angle measured from normal, and directing a second radiation beam having a second wavelength at the top surface of the substrate at a second angle measured from normal, wherein the second wavelength is not equal to the first wavelength. The method then comprises detecting scattered radiation from the first radiation beam and the second radiation beam to detect the presence of particles or COPs, and to differentiate between the two. Differences in the scattered radiation detected from the first radiation beam and from the second radiation beam provide the data needed to differentiate between particles and COPs.

75 Claims, 3 Drawing Sheets

U.S. PATENT DOCUMENTS

| | | |
|---|---|---|
| 4,893,932 A | 1/1990 | Knollenberg |
| 4,898,471 A | 2/1990 | Vaught et al. |
| 4,929,845 A | 5/1990 | Amir et al. |
| 4,966,457 A | 10/1990 | Hayano et al. ............ 356/237 |
| 5,058,982 A | 10/1991 | Katzir |
| 5,389,794 A | 2/1995 | Allen et al. |
| 5,416,594 A | 5/1995 | Gross et al. |
| 5,424,838 A | 6/1995 | Siu |
| 5,530,550 A | 6/1996 | Nikoonahad et al. |
| 5,623,341 A * | 4/1997 | Hunt ......................... 356/300 |
| 5,650,614 A | 7/1997 | Yasutake et al. |
| 5,798,829 A | 8/1998 | Vaez-Iravani |
| 6,104,481 A | 8/2000 | Sekine et al. |
| 6,201,601 B1 * | 3/2001 | Vaez-Iravani et al. ... 356/237.4 |
| 6,292,259 B1 | 9/2001 | Fossey et al. |
| 6,292,260 B1 | 9/2001 | Lin et al. ................. 356/237.4 |
| 6,509,964 B2 | 1/2003 | Wiles et al. |
| 6,587,192 B2 | 7/2003 | Isozaki et al. |
| 6,611,328 B2 | 8/2003 | Isozaki et al. |
| 6,654,111 B2 | 11/2003 | Isozaki et al. |

OTHER PUBLICATIONS

Figure, Hitachi Electronics Engineering Co., Ltd., presented by Etsuro Morita of Mitsubishi Materials Silicon, Corp. in a presentation entitled "Exploration of COP and COP Defect Crystal Originated 'Particles'," at the $6^{th}$ International Workshop on 300 Millimeter Wafers on Dec. 5, 1996 in Makuhari, Japan.

Partial European Search Report dated Oct. 18, 2000.

* cited by examiner

SYSTEMS AND METHODS FOR A WAFER INSPECTION SYSTEM USING MULTIPLE ANGLES AND MULTIPLE WAVELENGTH ILLUMINATION

CROSS REFERENCE TO RELATED APPLICATIONS

This application is a continuation-in-part of U.S. patent application Ser. No. 09/746,141, filed Dec. 21, 2000, now U.S. Pat. No. 6,639,662 which is a continuation of U.S. Pat. No. 6,201,601, issued Mar. 13, 2001 on an application Ser. No. 08/933,771, filed Sep. 19, 1997. Both of these documents are herein incorporated by reference.

BACKGROUND

1. Field of the Invention

The invention relates generally to the field of optical surface inspection, and more particularly, to illumination and light collection optics for inspecting semiconductor wafers, mask substrates, and other similar articles.

2. Background Information

Monitoring anomalies, such as pattern defects and particulate contamination, during the manufacture of unpatterned silicon wafers is an important factor in increasing production yields. Numerous types of defects and contamination, especially particles, can occur on a wafer's surface. Determining the presence, location and type of an anomaly on the wafer surface can aid in both locating process steps at which the anomaly occurred and determining whether a wafer should be discarded.

Originally, particles were monitored manually by visual inspection of wafer surfaces for the presence of particulate matter. These particles, usually dust or other microscopic particles, caused many of the wafer pattern defects. However, manual inspection proved time-consuming and unreliable due to operator errors or an operator's inability to observe certain defects.

To decrease the time required to inspect wafer surfaces, many automatic inspection systems were introduced. A substantial majority of these automatic inspection systems detect particles based on the scattering of radiation. These systems include two major components: illumination optics and collection-detection optics. Illumination optics generally consists of scanning a wafer surface with a coherent source of radiation, e.g., a laser. Particles present on the wafer's surface scatter incident radiation. The collection optics detect the scattered radiation with reference to the known beam position. The scattered radiation is then converted to electrical signals which can be measured, counted and displayed as bright spots on an oscilloscope or other monitor.

The sensitivity of systems that employ radiation to detect particles is based on a ratio of the photon flux detected by radiation striking a particle to the photon flux detected by radiation striking the surface of the wafer. The greater this ratio, the greater the sensitivity of the system. Therefore, many systems utilize radiation that is incident on the wafer's surface at an oblique angle. Obliquely incident radiation generates a larger ratio of photon flux from a particle to that from the surface of the wafer. These systems are then able to better detect smaller particles on a wafer surface.

Known sample inspection systems can detect particles as small as sixty nanometers in diameter while still gathering other data allowing them to differentiate between particles and crystal originated particles (also known as "COPs", which are surface breaking defects in a semiconductor wafer that were in the past classified as "particles" due to the inability of earlier inspection systems to distinguish them from real particles). An exemplary system of this type is the Surfscan® SP1$^{TB1}$ Wafer Inspection System by KLA-Tencor, Inc. of San Jose, Calif. The Surfscan® system uses two separate radiation beams to inspect a substrate, one radiation beam that is substantially normal to the sample surface, and one that is at an oblique angle in the range of 70 degrees from normal to the sample surface. The oblique radiation beam typically has a 488 nm wavelength. Although systems such as this one are available, it is desirable to provide sample inspection tools that can detect even smaller particles and COPs without compromising their ability to differentiate between particles and COPs. It is further desirable to provide inspection tools to detect defects that are strictly on the surface of semiconductor wafers and other samples, and to distinguish these from those defects that are within the samples.

SUMMARY

The limitations of known systems have been substantially improved upon by the present invention.

According to an embodiment of the invention, a method for detecting an anomaly on a top surface of a substrate comprises directing a first radiation beam having a first wavelength at the top surface of the substrate at a first angle measured from normal, and directing a second radiation beam having a second wavelength at the top surface of the substrate at a second angle measured from normal, wherein the second wavelength is not equal to the first wavelength. The method then comprises detecting radiation from the first radiation beam and the second radiation beam to detect the presence of particles or COPs, and to differentiate between the two. Particles and COPs are found when the detected radiation shows that the first radiation beam and/or the second radiation beam was scattered upon interacting with the top surface. Differences in the scattered radiation detected from the first radiation beam and from the second radiation beam provide the data needed to differentiate between particles and COPs.

In further embodiments of the invention, the first radiation beam can have a first wavelength that is in the ultraviolet region, in particular, around 266 nanometers. The second radiation beam can have a second wavelength that is in the visible radiation spectrum, in particular, around 532 nanometers. Use of a first radiation beam that is around 266 nanometers allows for the detection of smaller particles.

According to another embodiment of the invention, a system for detecting an anomaly on a top surface of a substrate comprises a radiation source operable to emit a first wavelength radiation and a second wavelength radiation, at least one objective operable to focus the first wavelength radiation into a first radiation beam and to focus the second wavelength radiation into a second radiation beam, and a detector mounted to detect radiation. The radiation source can be provided by a laser, in particular a solid-state laser, in some embodiments of the invention. And the detector can be mounted to detect scattered radiation that is created when the first and/or second radiation beams encounter an anomaly while directed at the surface of a substrate.

In other embodiments, the system can include at least one mirror mounted to direct the first radiation beam at the top surface at a first angle measured from normal and to direct the second radiation beam at the top surface at a second angle measured from normal. The system can also include curved mirrors that are operable to collect scattered radiation and focus that scattered radiation onto the detector.

A technical advantage of the invention includes the use of high frequency radiation, such as deep ultra-violet radiation, to detect particles that are relatively smaller than the particles detected by known systems.

A further advantage of the invention is that it provides, by virtue of the limited penetration depth of ultraviolet radiation into silicon, a method to detect only those defects confined to a top surface of a semiconductor wafer. Such an ability may be desirable, for example, in inspecting silicon-on-insulator (SOI) wafers, where the material of interest is often in the top, relatively thin, layer.

Yet another advantage of the invention is the ability to distinguish between defects on, or very close to, the surface of a wafer, and defects residing underneath the surface, by using multiple wavelengths of radiation having different penetration depths into the sample.

Another advantage of the invention is that it avoids inflicting damage upon delicate materials, such as some low-k dielectric materials, which may be rather intolerant of ultraviolet radiation, by utilizing alternate radiation wavelengths when such materials are present.

Other important technical advantages of the present invention are readily apparent to one skilled in the art from the following figures, descriptions, and claims.

BRIEF DESCRIPTION OF THE DRAWINGS

For a more complete understanding of the present invention and for further features and advantages, reference is now made to the following description taken in conjunction with the accompanying drawings, in which.

DETAILED DESCRIPTION

The embodiments of the present invention and their advantages are best understood by referring to FIGS. 1 through 5 of the drawings. Like numerals are used for like and corresponding parts of the various drawings.

Figure 1:
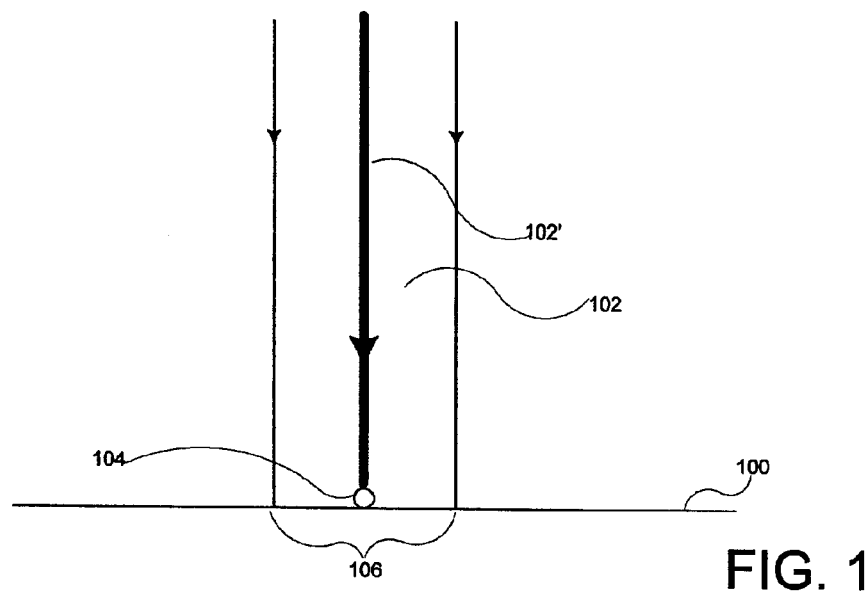
FIG. 1 illustrates a radiation beam directed at the surface of a substrate in a direction normal to the surface, wherein the radiation beam is striking a particle.

FIG. 1 is a schematic view of a surface 100 of a substrate being inspected by a radiation beam 102 for one or more particles 104. Here, radiation beam 102 is directed at surface 100 in a direction normal to the surface. Radiation beam 102 illuminates an area or spot 106 as it scans across surface 100 searching for particles 104. FIG. 1 illustrates a moment when radiation beam 102 encounters one particle 104 resting on surface 100, with a portion 102' of radiation beam 102 being in contact with particle 104. A detection system (shown in FIG. 4) then detects radiation scattered by particle 104 and by surface 100 at spot 106. The ratio of the photon flux received by the detector from particle 104 to that from spot 106 indicates the sensitivity of the system to particle detection.

Figure 2:
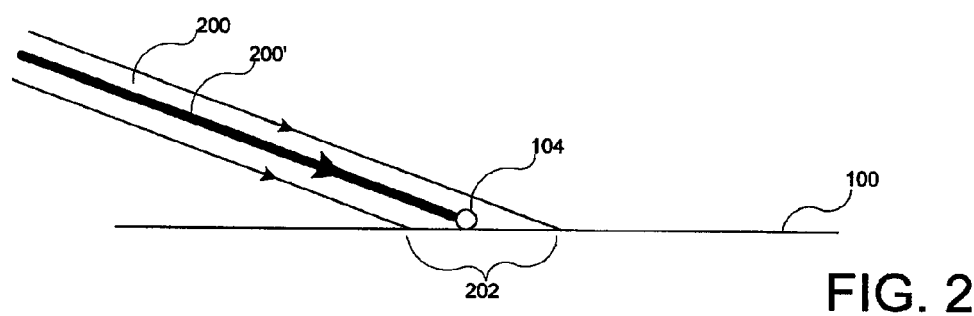
FIG. 2 illustrates a radiation beam directed at the surface of a substrate in a direction oblique to the surface, wherein the radiation beam is again striking a particle.

FIG. 2 is a schematic view of surface 100 being inspected again, but this time by an obliquely directed radiation beam 200 that illuminates a spot 202 on surface 100. A portion 200' of radiation beam 200 strikes particle 104. As shown by a comparison of FIGS. 1 and 2, it is evident that the particle-to-spot photon flux ratio will be greater in the case of the obliquely directed radiation beam 200 in FIG. 2 than in the case of the normally directed radiation beam 102 in FIG. 1.

Therefore, if radiation beam 102 and radiation beam 200 have the same throughput, and if the areas of spot 106 and spot 202 are the same, then the sensitivity of the system will be greater when using an obliquely directed radiation beam 200. As a result, the sensitivity of the obliquely incident radiation beam 200 in detecting small particles is superior and is the method of choice for the detection of small particles.

Figure 3:
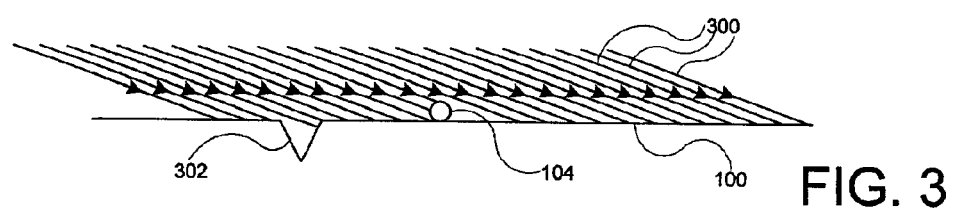
FIG. 3 illustrates radiation beams directed at the surface of a substrate in a direction oblique to the surface and striking a pit and a particle.

FIG. 3 illustrates a plurality of obliquely directed radiation beams 300 illuminating surface 100 having a COP 302 and particle 104 thereon. As can be seen from FIG. 3, even though COP 302 is a size that is comparable to particle 104, the portion of COP 302 that scatters radiation is much smaller than the portion of particle 104 that scatters radiation. As a result, COP 302 generates less scattered radiation than particle 104 when obliquely directed radiation beams 300 are used. Contrary to this, when normally directed radiation beams are used, such as radiation beam 102, COP 302 and particle 104 tend to generate comparable amounts of scattered radiation.

Thus, almost regardless of the exact shape or orientation of COPs and particles, anomaly detection employing obliquely directed radiation is much more sensitive to particles than COPs. In the case of anomaly detection with normally directed radiation, however, the differentiation between particles and COPs is less pronounced. Therefore, inspecting a substrate using both obliquely directed radiation and normally directed radiation (either simultaneously or sequentially), and then comparing the data gathered from each, will reveal whether any anomaly found is a particle or a COP.

Figure 4:
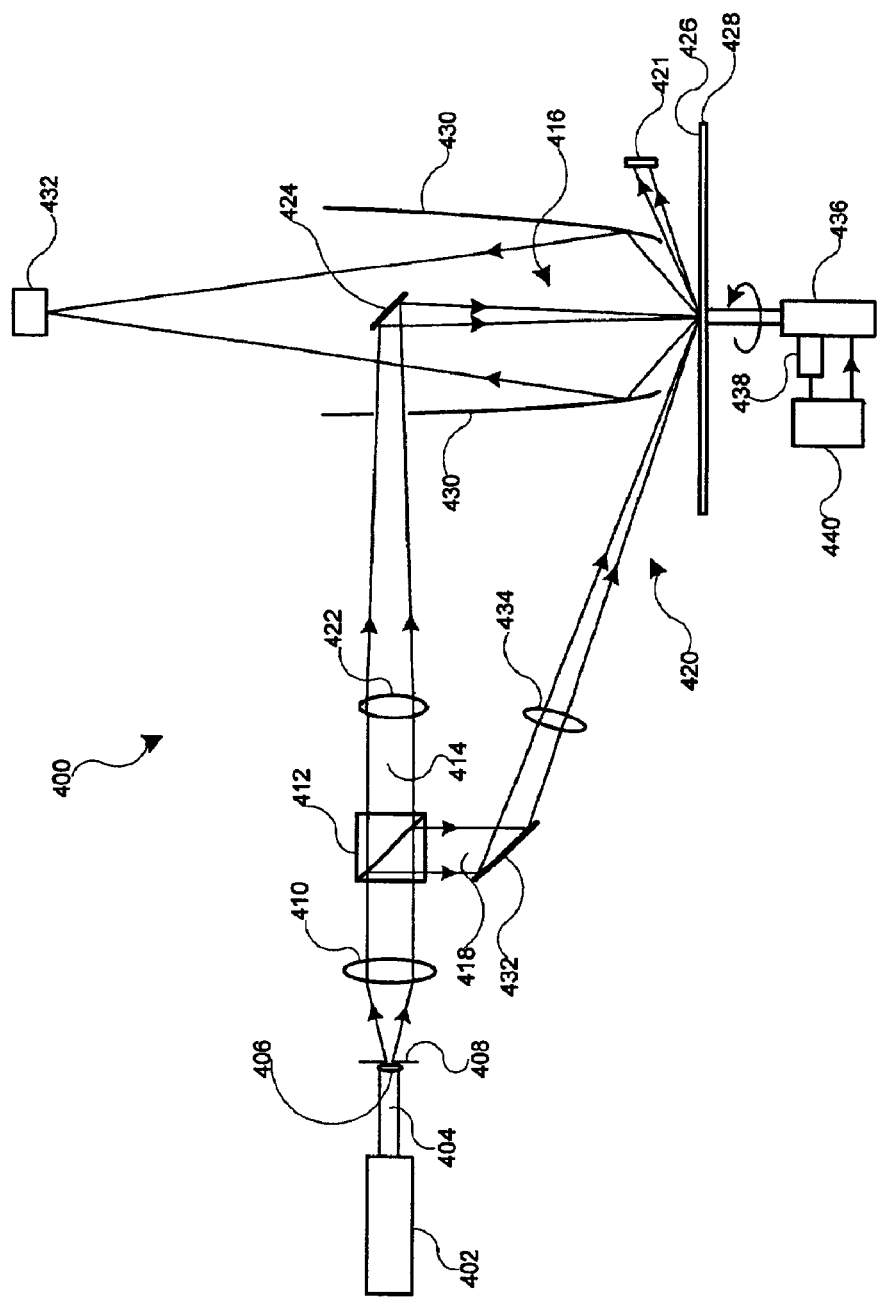
FIG. 4 is a schematic diagram of a wafer inspection system in accordance with an embodiment of the invention.

FIG. 4 is a schematic view of a sample inspection system 400 according to an embodiment of the invention. This embodiment illustrates one way to implement anomaly detection using both normal and oblique radiation beams. And as is explained below, the normal and oblique radiation beams can be used simultaneously in system 400.

Sample inspection system 400 includes a radiation source 402 that operates to emit a radiation beam 404 at two or more wavelengths. In one embodiment, a device that can be used as radiation source 402 can be a solid-state laser. Solid-state lasers tend to be more stable, reliable, and compact than other types of lasers, making them attractive for use in sample inspection systems. In particular, a YAG solid-state laser can be used as radiation source 402. Through a process called harmonic laser light generation, the fundamental radiation wavelength at 1064 nm can be doubled, tripled, or quadrupled, by passing it through some crystals, to generate light in the visible (at around 532 nm), ultraviolet (at around 355 nm), and deep ultraviolet (at around 266 nm) regions. In other embodiments of the invention, radiation source 402 can be provided by these alternative laser sources, including Argon Ion lasers.

During harmonic laser light generation, a portion of the radiation passing through the crystals is not converted to a new frequency. For example, in a 266 nm laser system, a large portion of radiation remains unconverted at 532 nm. Typically this unconverted radiation would be rejected at the output so that the actual emitted radiation beam 404 from the laser source is at a single frequency. In an embodiment of the invention however, this unconverted radiation can be put to use as either the normal or the oblique radiation beam in a wafer inspection system. In various embodiments, the unconverted radiation can be made available either through the same exit port as the emitted radiation or through a separate exit port. In the embodiment shown in FIG. 4, the unconverted radiation can be output through the same exit port as the emitted radiation. So for the particular 266 nm laser system mentioned above, emitted radiation beam 404 would now consist of 266 nm radiation and 532 nm radiation. In alternative embodiments, emitted radiation beam 404 from radiation source 402 can consist of other combinations of frequencies, such as 266 nm radiation with 355 nm radiation, or 355 nm radiation with 532 nm radiation.

After radiation beam 404 passes through objective 406 and filter 408 of the spatial filter, a collimating objective 410 collimates radiation beam 404 and directs it to a beam splitter 412. Beam splitter 412 passes a first radiation component 414 of radiation beam 404 to a normal illumination channel 416, and a second radiation component 418 to an oblique illumination channel 420. In other words, illumination channel 416 is at around zero degrees to a normal direction to surface 426. According to an embodiment of the invention, first radiation component 414 and second radiation component 418 have different wavelengths. Therefore, beam splitter 412 passes radiation at a first wavelength on to normal illumination channel 416, and passes radiation at a second wavelength on to oblique illumination channel 420.

In accordance with an embodiment of the invention, ultraviolet or deep-ultraviolet radiation is used in oblique illumination channel 420. In particular, radiation around 266 nm can be used in oblique illumination channel 420. The use of 266 nm radiation, due to its shorter wavelength, enhances the sensitivity of sample inspection system 400 to particles that scatter radiation through wavelength scaling laws as taught by Mie/Rayleigh scattering. Thus, to ensure as great an impact as possible on the scattering signal, one must use as short a wavelength as possible. This enhanced sensitivity to particles that scatter radiation in turn makes detection of even smaller particles possible. And since the use of shorter wavelength radiation is intended to aid in detecting particles, it makes the most sense to use the shorter wavelength radiation in the oblique illumination channel, which is more sensitive to particles than to COPs.

Another advantage to using ultraviolet radiation is that only a shallow region of the semiconductor wafer can be inspected. This is because there is limited penetration of ultraviolet radiation in silicon, and therefore the inspection area is generally confined to just the surface of the semiconductor wafer. So in those instances where one may be interested in detecting defects only on the top surface of the wafer, inspection of the semiconductor wafer can be performed using ultraviolet radiation.

In other instances where one may be interested in detecting and distinguishing all defects on a wafer, regardless of whether they are at or below the wafer surface, the invention can utilize ultraviolet radiation in combination with visible radiation. Unlike ultraviolet and deep ultraviolet radiation, visible radiation can penetrate a greater amount into the semiconductor wafer. So a wafer can be simultaneously, or sequentially, inspected by both ultraviolet radiation and visible radiation, and a comparison of the data gathered from the two radiation wavelengths can discern whether defects are at or below the wafer surface.

According to an embodiment of the invention, visible spectrum radiation, in particular 532 nm radiation, can be used in normal illumination channel 416. Since known systems typically use visible spectrum radiation, the use of visible 532 nm green light in normal illumination channel 416 will generally allow these known systems to implement the teachings of the invention with minimal changes to optical components along normal illumination channel 416. 532 nm radiation can be used in normal illumination channel 416 while 266 nm (or 355 nm) radiation can be used in oblique illumination channel 420.

It should be noted that for inspecting low-K dielectric films, sample inspection system 400 will generally not employ 266 nm radiation in either oblique illumination channel 420 or normal illumination channel 416, as there is some likelihood of sample damage. 355 nm radiation may be less damaging to some of these delicate layers. To avoid such issues, visible radiation such as 532 nm radiation can be employed in both channels.

In another embodiment of the invention, first radiation component 414 and second radiation component 418 have the same wavelength. For example, the wavelength of both first radiation component 414 and second radiation component 418 can be in the deep-ultraviolet range, around 266 nm. Radiation at 266 nm is preferable because as explained above, the shorter wavelength of this radiation causes system 400 to attain enhanced sensitivity to smaller particles.

In an embodiment of the invention, beam splitter 412 can be provided by a dichroic filter or a dichroic mirror. A dichroic filter is a filter used to selectively transmit radiation according to its wavelength and not its plane of vibration, and is generally used for normal incidence. A dichroic mirror on the other hand is designed to reflect a specific wavelength region and transmit other regions, and is normally used for non-normal incidence. By correctly positioning either the dichroic filter or the dichroic mirror, first radiation component 414 of radiation beam 404 can be transmitted to normal illumination channel 416, and second radiation component 418 of radiation beam 404 can be reflected to oblique illumination channel 420.

As noted above, radiation beam 404 can include 266 nm radiation and 532 nm radiation. So in one embodiment of the invention, the dichroic filter or mirror can be mounted to pass 532 nm radiation as first radiation component 414 to normal illumination channel 416, and pass 266 nm radiation as second radiation component 418 to oblique illumination channel 420. And when radiation beam 404 includes 266 nm radiation and 355 nm radiation, the 355 nm radiation can be passed as first radiation component 414 to normal illumination channel 416. In alternate embodiments, beamsplitter 412 can be provided by a high pass filter, a low pass filter, or a band pass filter.

After radiation beam 404 is broken into first radiation component 414 and second radiation component 418 by beamsplitter 412, according to one embodiment, first radiation component 414 can be focused by an objective 422 and reflected by a mirror 424 into normal illumination channel 416. First radiation component 414 then strikes a surface 426 of a semiconductor wafer 428 being inspected by system 400. The radiation from first radiation component 414 that is scattered by surface 426 can then be collected by a collection system 430, provided in this embodiment by an ellipsoidal mirror. The scattered radiation can also be focused by collection system 430 onto a detector 432. In an embodiment, detector 432 can be provided by a photomultiplier tube. Other detector types include avalanche photodiodes (APD), enhanced for responsivity in the shorter wavelength range.

According to an embodiment, second radiation component 418 is reflected off beamsplitter 412 to a mirror 432, which then reflects second radiation component 418 to an objective 434. Second radiation component 418 can be focused by objective 434 into oblique illumination channel 420. Second radiation component 418 then strikes surface 426 at an oblique angle, and in an embodiment, this angle can be around 70 degrees measured from normal. An angle of 70 degrees is advantageous because known systems generally use a 70 degree angle for obliquely directed radiation. This again helps minimize any modifications required if the invention is implemented into known systems. As radiation from second radiation component strikes surface 426, the scattered radiation that is generated is collected by collection system 430 and focused onto detector 432.

The optics in both normal illumination path 416 and oblique illumination path 420 can be such that they create illuminated spots on surface 426 that substantially overlap with no offset there between. The radiation scattered by surface 426 retains the wavelength characteristics of first and second radiation components 414 and 418 from which the radiation originates, so that the radiation scattered by surface 426 originating from first radiation component 414 can be separated from radiation scattered by surface 426 originating from second radiation component 418. So detector 432 can receive scattered radiation from both first radiation component 414 and second radiation component 418 simultaneously, and can then separate them to generate an independent data set for each radiation component. Accordingly, due to the fact that two different wavelengths of radiation are used in normal illumination path 416 and oblique illumination path 420, system 400 can inspect surface 426 with both normal and oblique illumination paths simultaneously.

As shown in FIG. 4, semiconductor wafer 428 can be rotated by a motor 436 which can also be moved linearly by a transducer 438, and both movements can be controlled by a controller 440, so that first and second radiation components 414 and 418 in normal and oblique illumination channels 416 and 418 can scan surface 426 along a spiral scan to cover the entire surface.

In an embodiment of the invention, if laser source 402 is emitting 266 nm (or 355 nm) radiation and 532 nm radiation, collection system 430 can be optimized to reflect 266 nm radiation to detector 432. Due to the intensity of 532 nm radiation, collection system 430 does not have to have a particularly high reflectance at 532 nm because enough of that radiation will still reach detector 432. Therefore, one collection system 430 can be used for both wavelengths of radiation used by system 400.

In alternate embodiments of the invention, instead of using an ellipsoidal mirror as in collection system 430, other curved mirrors can be used, including but not limited to a paraboloidal mirror. A paraboloidal mirror will collimate the scattered radiation from surface 426 into a collimated beam, and this collimated beam can then be focused by an objective to a detector. Curved mirrored surfaces having shapes other than ellipsoidal or paraboloidal shapes may also be used. Preferably, each of such curved mirrored surfaces has an axis of symmetry substantially coaxial with the path of normal illumination channel 416, and defines an input aperture for receiving scattered radiation. All such variations are within the scope of the invention.

Figure 5:
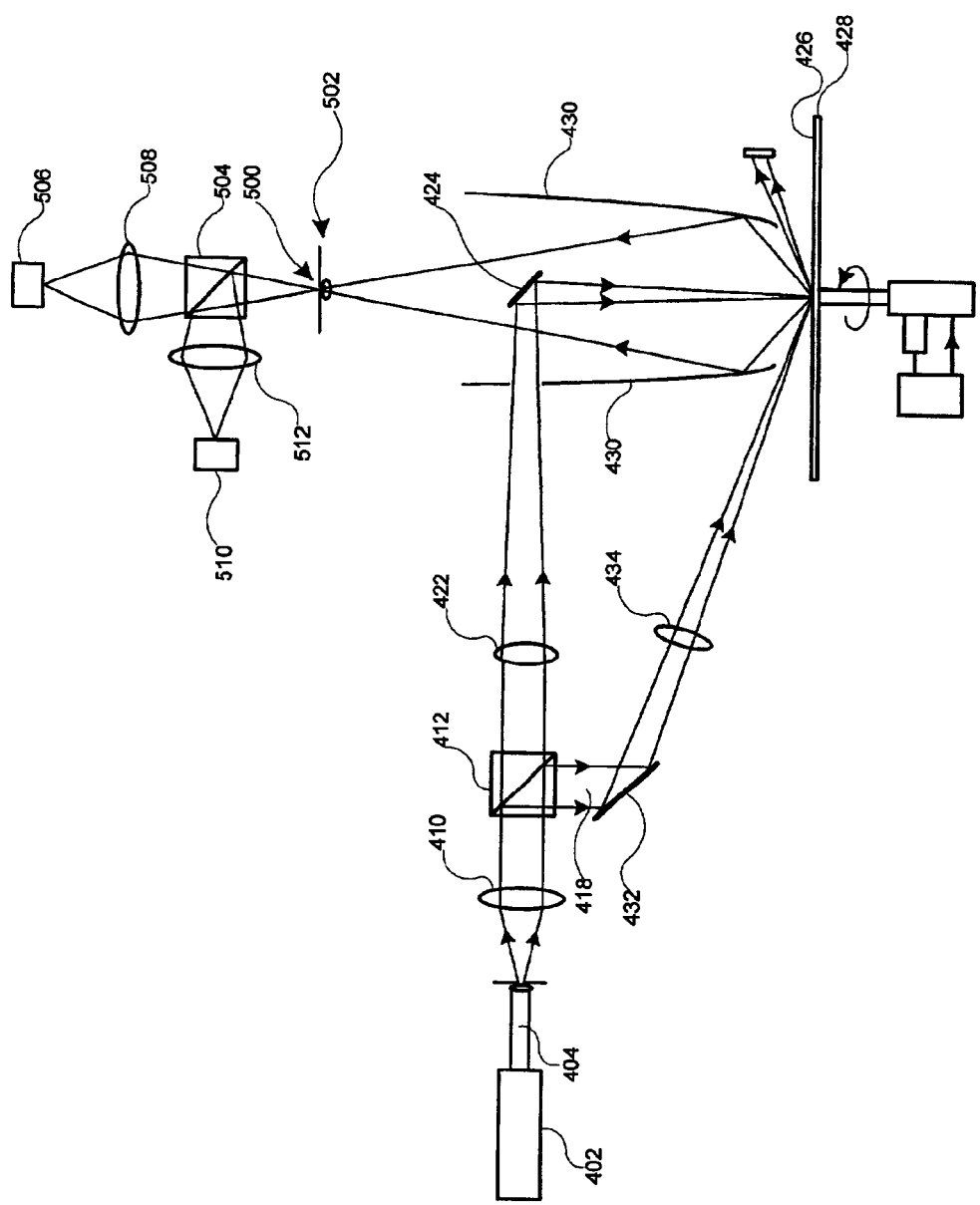
FIG. 5 a schematic diagram of a wafer inspection system in accordance with an alternative embodiment of the invention.

FIG. 5 illustrates an alternative embodiment of the invention where separate detectors are provided for each wavelength of scattered radiation. Radiation scattered by surface 426 can be collected and focused by collection system 430 through a pinhole 500 of a spatial filter 502 to a beamsplitter 504. In the embodiment of FIG. 5, beamsplitter 504 can be provided by a dichroic filter or a dichroic mirror. Beamsplitter 504 transmits scattered radiation at a first wavelength to a detector 506 through an objective 508, and reflects scattered radiation at a second wavelength to a detector 510 through an objective 512. The first wavelength scattered radiation can originate from first radiation component 414, and the second wavelength scattered radiation can originate from second radiation component 418.

The general arrangements shown in FIGS. 4 and 5 can be implemented in different embodiments. In one embodiment, first radiation component 414 and second radiation component 418 can be scanned across surface 426 sequentially rather than simultaneously. This can be done where only one detector 432 is being used, and that detector is incapable of separating different wavelengths of radiation. In this embodiment, during a first cycle system 400 passes radiation only into normal illumination channel 416 and no radiation is directed towards oblique illumination channel 420. Then during a second cycle, system 400 reflects radiation only into oblique illumination channel 420 and no radiation is directed through normal illumination channel 416. During the first cycle detector 432 only collects radiation from normal illumination channel 416, and during the second cycle detector 432 only collects radiation from oblique illumination channel 420. This is typically performed for the entire surface 426. As long as the scan in the first cycle and the scan in the second cycle are exactly registered, the data sets collected during the first and second cycles can be compared to provide information concerning the nature of the defects detected.

System 400 can pass only one wavelength of radiation at a time by using a beamsplitter that can selectively pass or reflect radiation, or by providing other elements such as a removable mirror placed in the position of beamsplitter 412. If the mirror is not present, radiation from radiation source 402 is directed along the normal illumination channel 416. When the mirror is present, the radiation is then directed along the oblique illumination channel 420. In another embodiment, removable band pass filters can be used to select radiation. One band pass filter can be used to block second radiation component 418 when first radiation component 414 is being used to inspect surface 426 along normal illumination channel 416, and another band pass filter can be used to block first radiation component 414 when second radiation component 418 is being used to inspect surface 426 along oblique illumination channel 420. In other embodiments of the invention, alternative techniques or elements can be used to effectuate this sequential method of inspecting surface 426.

Accordingly, systems and methods of the invention have been described for a wafer inspection system using multiple angles and multiple wavelength illumination. Unlike previously developed techniques in which a single wavelength radiation is used to inspect a wafer surface by first providing normally incident radiation, and then separately providing obliquely incident radiation, the systems and methods of the present invention utilize two different wavelengths of radiation that can simultaneously inspect a wafer surface in both the normal and the oblique directions. In addition, the systems and methods of the invention use ultraviolet or deep-ultraviolet radiation, around 355 or 266 nm, in the oblique illumination path to enhance particle sensitivity and aid in the detection of smaller particles. Furthermore, the use of visible spectrum radiation, such as 532 nm radiation, in the normal illumination path minimizes changes to optical elements in the normal path in known systems and preserves the primary uses of the normally incident radiation. In addition, the system can be utilized in such a way as to avoid possible damage to delicate layers due to exposure to ultraviolet radiation, by ensuring that such layers are inspected by visible radiation only. In such cases, provision is made sequentially to direct the visible radiation into both normal and oblique paths. The system allows for the inspection of silicon-on-insulator (SOI) wafers, and classification of the defects above and below the surface. Finally, currently available laser sources can be used in the invention, although they may require modification.

While various embodiments of the invention have been shown and described, it will be apparent to those skilled in the art that numerous alterations may be made without departing from the inventive concepts presented herein. Thus, the invention is not to be limited except in accordance with the following claims and their equivalents.

What is claimed is:

1. A method for detecting an anomaly on a top surface of a substrate, or within the substrate, comprising:
    directing a first radiation beam having a first ultraviolet or deep ultraviolet wavelength to illuminate a first spot on the top surface of the substrate at a first non-zero angle measured from a normal direction to the top surface;
    directing a second radiation beam having a second wavelength to illuminate a second spot on the top surface of the substrate at a second angle measured from a normal direction to the top surface, wherein the second wavelength is greater than the first wavelength, so that radiation from the second beam penetrates the surface of the substrate by a distance greater than that by radiation from the first beam;
    causing relative motion between the first and second radiation beams and the top surface of the substrate so that the spots scan paths on the top surface;
    detecting radiation from the first radiation beam scattered by the top surface in the first spot to provide a single output corresponding to a position of the first spot on the top surface;
    detecting radiation from the second radiation beam scattered by the top surface in the second spot to provide a single output corresponding to a position of the second spot on the top surface; and
    generating from the outputs first data set(s) containing only data on anomalies at or substantially at the surface of the substrate and second data set(s) containing data on anomalies away from the surface of the substrate, so that anomalies at or substantially at the surface of the substrate are detectable independently from anomalies away from the surface of the substrate from the data sets.

2. The method of claim 1, further comprising documenting the presence of an anomaly if the detected radiation shows that the first radiation beam was scattered upon interacting with the top surface.

3. The method of claim 1, further comprising documenting the presence of an anomaly if the detected radiation shows that the second radiation beam was scattered upon interacting with the top surface.

4. The method of claim 1, further comprising comparing radiation detected from the first radiation beam to radiation detected from the second radiation beam to determine whether the anomaly comprises a COP or a particle.

5. The method of claim 1, wherein the first wavelength is around 266 nanometers.

6. The method of claim 1, wherein the first wavelength is around 355 nanometers.

7. The method of claim 1, wherein the first wavelength is a wavelength in the ultraviolet spectrum of radiation.

8. The method of claim 1, wherein the second wavelength is around 532 nanometers.

9. The method of claim 1, wherein the second wavelength is a wavelength in the visible spectrum of radiation.

10. The method of claim 1, wherein the first wavelength is around 266 nanometers and the second wavelength is around 532 nanometers.

11. The method of claim 1, wherein the first wavelength is around 355 nanometers and the second wavelength is around 532 nanometers.

12. The method of claim 1, wherein the first wavelength is in the ultra-violet spectrum of radiation and the second wavelength is in the visible spectrum of radiation.

13. The method of claim 1, wherein the first angle is around 70 degrees to a normal direction to the top surface.

14. The method of claim 1, wherein the second angle is around zero degrees to a normal direction to the top surface.

15. The method of claim 1, wherein the directing of a first radiation beam and the directing of a second radiation beam are performed simultaneously.

16. The method of claim 1, wherein the detecting of radiation from the first radiation beam and the detecting of radiation from the second radiation beam are performed simultaneously.

17. The method of claim 1, wherein the first radiation beam comprises a laser beam.

18. The method of claim 1, wherein the second radiation beam comprises a laser beam.

19. The method of claim 1, wherein the detecting of radiation from the second radiation beam comprises detecting scattered radiation from the second radiation beam and avoiding reflected radiation from the second radiation beam.

20. The method of claim 1, further comprising documenting the presence of an anomaly if the detected radiation shows an increase in the amount of scattered radiation produced by the first radiation beam.

21. The method of claim 1, further comprising documenting the presence of an anomaly if the detected radiation shows an increase in the amount of scattered radiation produced by the second radiation beam.

22. The method of claim 1, further comprising comparing radiation detected from the first radiation beam to radiation detected from the second radiation beam to determine whether the anomaly is located on tho top surface or below the top surface of the substrate.

23. The method of claim 1, wherein said directing directs the beam to the surface of an unpatterned semiconductor wafer.

24. The method of claim 1, further comprising registering the scan paths of the spots illuminated by the first and second radiation beams.

25. A method for detecting an anomaly on a top surface of a substrate, or within the substrate, comprising:
    directing a first radiation beam having a first wavelength to illuminate a first spot on the top surface of the substrate at a first non-zero angle measured from normal, wherein the first wavelength is in the ultraviolet or deep ultraviolet spectrum of radiation;

directing a second radiation beam having a second wavelength to illuminate a second spot on the top surface of the substrate at a second angle measured from normal, wherein the second wavelength is in the visible spectrum of radiation;

detecting radiation from the first and second radiation beams;

causing relative motion between the first and second radiation beams and the top surface of the substrate, so that the spots scan paths on the top surface, wherein said detecting detects radiation scattered by the top surface to provide one or more outputs;

generating from the outputs first data set(s) containing only data on anomalies at or substantially at the surface of the substrate and second data set(s) containing data on anomalies away from the surface of the substrate, so that anomalies at or substantially at the surface of the substrate are detectable independently from anomalies away from the surface of the substrate from the data sets; and documenting the presence of an anomaly if the data sets shows an increase in the amount of scattered radiation produced by the first radiation beam or the second radiation beam.

26. The method of claim 25, wherein said directing directs the beam to the surface of a silicon-on-insulator or unpatterned semiconductor wafer, and the detecting detects radiation scattered by the silicon-on-insulator or unpatterned semiconductor wafer.

27. A system for detecting an anomaly on a top surface of a substrate, or within the substrate, comprising:

a device providing a first wavelength radiation and a second wavelength radiation to illuminate the top surface, said first wavelength being ultraviolet or deep ultraviolet;

optics focusing the first wavelength radiation into a first radiation beam at an oblique first angle to the top surface to illuminate a first spot on the top surface and focusing the second wavelength radiation into a second radiation beam at a second angle to a normal direction to top surface to illuminate a second spot on the top surface, wherein the second wavelength is greater than the first wavelength, so that radiation of the second wavelength penetrates the surface of the substrate by a distance greater than that by radiation of the first wavelength;

means for causing relative motion between the first and second radiation beams and the top surface of the substrate, so that the spots scan paths on the top surface; and a detector mounted to detect radiation scattered by the top surface in the first or second spot to provide a first single output in response to the scattered radiation in the first beam corresponding to a position of the first spot on the top surface in one of the scan paths, and a second single output in response to the scattered radiation in the second beam corresponding to a position of the second spot on the top surface in one of the scan paths; and means for generating from the outputs first data set(s) containing only data on anomalies at or substantially at the surface of the substrate and second data set(s) containing data on anomalies away from the surface of the substrate, so that anomalies at or substantially at the surface of the substrate are detectable independently from anomalies away from the surface of the substrate from the data sets.

28. The system of claim 27, further comprising a beamsplitter to separate the first radiation beam from the second radiation beam.

29. The system of claim 28, further comprising at least one mirror mounted to direct the first radiation beam at the top surface and to direct the second radiation beam at the top surface.

30. The system of claim 28, wherein the first beam is around 70 degrees measured from a normal direction to the top surface.

31. The system of claim 28, wherein the second angle is around zero degrees from a normal direction to the top surface.

32. The system of claim 27, further comprising a collector that is rotationally symmetric about a line and that is operable to collect radiation and focus the radiation onto the detector.

33. The system of claim 27, wherein the radiation source is provided by a laser source.

34. The system of claim 33, wherein the laser source is a solid-state laser.

35. The system of claim 33, wherein the laser source can vary the wavelength of emitted radiation using one or more crystals.

36. The system of claim 27, wherein the first wavelength is around 266 nanometers.

37. The system of claim 27, wherein the first wavelength is around 355 nanometers.

38. The system of claim 27, wherein the second wavelength is around 532 nanometers.

39. The system of claim 27, wherein the second wavelength is a wavelength in the visible spectrum of radiation.

40. The system of claim 27, wherein the first wavelength is around 266 nanometers and the second wavelength is around 532 nanometers.

41. The system of claim 27, wherein the first wavelength is around 355 nanometers and the second wavelength is around 532 nanometers.

42. The system of claim 27, wherein the first wavelength is a wavelength in the ultraviolet spectrum of radiation and the second wavelength is a wavelength in the visible spectrum of radiation.

43. A method for detecting an anomaly on a surface of a substrate, or within the substrate, comprising:

directing a first radiation beam to illuminate a first spot on the surface of the substrate at an oblique angle to the surface, said first beam having a ultraviolet or deep ultraviolet first wavelength;

directing a second radiation beam having a second wavelength to illuminate a second spot on the surface of the substrate at a second angle measured from the normal direction to the surface, wherein the second wavelength is greater than the first wavelength, so that radiation from the second beam penetrates the surface of the substrate by a distance greater than that by radiation from the first beam;

causing relative motion between the first and second radiation beams and the surface of the substrate so that the beams scans paths on the surface;

detecting radiation from the first and second radiation beams scattered by the surface in the spots to provide one or more outputs in response to the scattered radiation in the beams; and generating from the outputs first data set(s) containing only data on anomalies at or substantially at the surface of the substrate and second data set(s) containing data on anomalies away from the surface of the substrate, so that anomalies at or substantially at the surface of the substrate are detectable independently from anomalies away from the surface or the substrate from the data sets.

44. The method of claim 43, wherein said causing causes rotational and translational relative motion between the first radiation beam and the surface of the substrate.

45. The method of claim 43, further comprising comparing radiation detected from the first radiation beam to radiation detected from the second radiation beam to determine whether the anomaly comprises a COP or a particle.

46. The method of claim 43, wherein the second wavelength is around 532, 266 or 355 nanometers.

47. The method of claim 43, wherein the second wavelength is a wavelength in the visible spectrum of radiation.

48. The method of claim 43, wherein the first wavelength is around 266 or 355 nanometers and the second wavelength is around 532 nanometers.

49. The method of claim 43, wherein the first wavelength is in the ultra violet spectrum of radiation and the second wavelength is in the visible spectrum of radiation.

50. The method of claim 43, wherein the second angle is around zero degrees.

51. The method of claim 43, wherein the directing of a first radiation beam and the directing of a second radiation beam are performed sequentially or simultaneously.

52. The method of claim 43, wherein the detecting of radiation from the first radiation beam and the detecting of radiation from the second radiation beam are performed simultaneously.

53. The method of claim 43, wherein the detecting of radiation from the second radiation beam comprises detecting scattered radiation from the second radiation beam and avoiding reflected radiation from the second radiation beam.

54. The method of claim 43, further comprising documenting the presence of an anomaly if the detected radiation shows an increase in the amount of scattered radiation produced by the second radiation beam.

55. The method of claim 43, wherein said directing directs the second beam to a low-k dielectric material, said second beam containing a wavelength in a visible range.

56. The method of claim 43, further comprising comparing radiation detected from the first radiation beam to radiation detected from the second radiation beam to determine whether the anomaly is located on the top surface or below the top surface of the substrate.

57. The method of claim 43, wherein the relative motion causes the second radiation beam to scan a path on the surface, said method further comprising registering the scan paths of the spots illuminated by the first and second radiation beams.

58. The method of claim 43, further comprising documenting the presence of an anomaly if the detected radiation shows an increase in the amount of scattered radiation produced by the first radiation beam.

59. The method of claim 43, wherein the first beam is at an angle of around 70 degrees from a normal direction to the surface.

60. The method of claim 43, further comprising collecting radiation from the first radiation beam scattered by the surface in the spot by means of a radiation collector having an axis of rotational symmetry about a line, said collector focusing scattered radiation from the surface to the detector to produce the single output.

61. The method of claim 43, wherein said directing directs the beam to the surface of a silicon-on-insulator wafer, and the detecting detects radiation scattered by the silicon-on-insulator wafer.

62. The method of claim 43, wherein said directing directs the beam to the surface of an unpatterned semiconductor wafer.

63. An apparatus for detecting an anomaly on a surface of a substrate, or within the substrate, comprising:

optics directing a first radiation beam to illuminate a first spot on the top surface of the substrate at an oblique angle to the surface, said first beam having a ultraviolet or deep first ultraviolet wavelength;

optics directing a second radiation beam having a second wavelength to illuminate a second spot on the surface of the substrate at a second angle measured from the normal direction to the surface, wherein the second wavelength is grater than the first wavelength, so that radiation from the second beam penetrates the surface of the substrate by a distance greater than that by radiation from the first beam;

means for causing relative motion between the first and second radiation beams and the surface of the substrate so that the beams scans paths on the surface; and a detector detecting radiation from the first and second radiation beams scattered by the surface in the spots to provide one or more outputs in response to the scattered radiation in the beams; and means for generating from the outputs first data set(s) containing only data on anomalies at or substantially at the surface of the substrate and second data set(s) containing data on anomalies away from the surface of the substrate, so that anomalies at or substantially at the surface of the substrate are detectable independently from anomalies away from the surface of the substrate from the data sets.

64. The apparatus of claim 63, wherein said causing means comprises an instrument that causes rotational and translational relative motion between the first radiation beam and the surface of the substrate.

65. The apparatus of claim 63, further comprising means for comparing radiation detected from the first radiation beam to radiation detected from the second radiation beam to determine whether the anomaly comprises a COP or a particle.

66. The system of claim 63, further comprising a beamsplitter to separate the first radiation beam from the second radiation beam.

67. The system of claim 63, wherein the first wavelength is around 266 or 355 nanometers and the second wavelength is around 532 nanometers.

68. The system of claim 63, wherein the first wavelength is a wavelength in the ultraviolet spectrum of radiation and the second wavelength is a wavelength in the visible spectrum of radiation.

69. The system of claim 68, further comprising at least one mirror mounted to direct the first radiation beam at the surface at a first angle measured from normal and to direct the second radiation beam at the surface at a second angle measured from normal.

70. The system of claim 63, wherein the second angle is around zero degrees.

71. The system of claim 63, further comprising a collector having an axis of rotational symmetry about a line, said collector receiving and directing scattered radiation to the detector to produce the single output.

72. The system of claim 63, wherein the optics comprises a leaser source.

73. The system of claim 63, wherein the first wavelength is around 266 or 355 nanometers.

74. The system of claim 63, wherein the first beam is at an angle of around 70 degrees form a normal direction to the surface.

75. The system of claim 63, wherein the optics comprises a solid-state laser.

* * * * *